(12) United States Patent
Friel et al.

(10) Patent No.: US 8,518,894 B2
(45) Date of Patent: Aug. 27, 2013

(54) HUMAN MILK PEPTIDES

(75) Inventors: Kenneth James Friel, Winnipeg (CA); Apollinaire Tsopmo, Nepean (CA)

(73) Assignees: Kenneth James Friel, Winnipeg, MB (CA); Apollinaire Tsopmo, Nepean, ON (CA)

( * ) Notice: Subject to any disclaimer, the term of this patent is extended or adjusted under 35 U.S.C. 154(b) by 0 days.

(21) Appl. No.: 13/375,319

(22) PCT Filed: Jun. 1, 2010

(86) PCT No.: PCT/CA2010/000804
§ 371 (c)(1),
(2), (4) Date: Feb. 29, 2012

(87) PCT Pub. No.: WO2010/139048
PCT Pub. Date: Dec. 9, 2010

(65) Prior Publication Data
US 2012/0157372 A1    Jun. 21, 2012

Related U.S. Application Data

(60) Provisional application No. 61/182,840, filed on Jun. 1, 2009.

(51) Int. Cl.
*A61K 38/16* (2006.01)
*A61K 38/10* (2006.01)
*A61K 38/08* (2006.01)

(52) U.S. Cl.
USPC ....... 514/21.7; 514/21.8; 514/21.6; 514/21.5; 514/21.4; 514/21.3

(58) Field of Classification Search
None
See application file for complete search history.

(56) References Cited

U.S. PATENT DOCUMENTS

| | | | |
|---|---|---|---|
| 5,773,245 A | 6/1998 | Wittrup et al. | |
| 5,942,274 A * | 8/1999 | Slattery | 426/580 |
| 7,834,146 B2 | 11/2010 | Kovalic et al. | |
| 2003/0027309 A1 | 2/2003 | Pompejus et al. | |
| 2004/0031072 A1 | 2/2004 | La Rosa et al. | |
| 2005/0048574 A1* | 3/2005 | Kantor et al. | 435/7.1 |
| 2006/0123505 A1 | 6/2006 | Kikuchi et al. | |
| 2007/0142292 A1 | 6/2007 | Varadhachary et al. | |
| 2009/0270309 A1 | 10/2009 | Cornish et al. | |

FOREIGN PATENT DOCUMENTS

| | | |
|---|---|---|
| JP | 2003319300 | 11/2000 |
| WO | WO 94/08012 | 4/1994 |
| WO | WO 94/12640 A1 | 6/1994 |
| WO | WO 01/32677 A1 | 5/2001 |
| WO | WO 02/094981 A2 | 11/2002 |
| WO | WO 2004/091548 A2 | 10/2004 |
| WO | WO 2007/043900 A1 | 4/2007 |
| WO | WO 2008/008766 A2 | 1/2008 |

OTHER PUBLICATIONS

Cervato, G., et al., Studies on the antioxidant activity of milk caseins, Int. J. Food Sci. Nutr., vol. 50, No. 4, 291-296 (1999).
Database NCBI, Accession No. Q5K2C6, Jun. 7, 2005.
International Search Report for International Patent Application No. PCT/CA2010/000804 filed on Jun. 1, 2010.
Written Opinion for International Patent Application No. PCT/CA2010/000804 filed on Jun. 1, 2010.
Friel, J.K. et al., "BioAvailability of Human Milk Derived Peptides using a CACO-2 Cell Culture Model", BioAvailability Conference, Asilomar, CA, Sep. 26-30, 2010.
Friel, J.K. et al., "Anti-inflammatory, anti-oxidant, anti-microbial properties of human milk derived peptides", Abstract, FASEB J, Apr. 6, 2010.
Tani, F. et al., "Isolation and Characterization of Opioid Antagonist Peptides Derived from Human Lactoferrin", Agric. Biol. Chem, 54 (7), 1803-1810, 1990.
Miloudi, K. et al., "Hexapeptides from human milk prevent the induction of oxidative stress from parenteral nutrition in the newborn guinea pig", Pediatric Research, 71(6): 675-681, (Mar. 21, 2012).
Tsopmo, Apollinarire et al., "Novel anti-oxidative peptides from enzymatic digestion of human milk", Food Chemistry 126, 1138-1143 (Dec. 1, 2010).
Beleid, R., et al., "Helical peptides derived from lactoferrin bind Hepatitis C virus envelope protein E2", Chem. Biol. Drug Des., (2008), 72, 436-443.
Diehl-Jones, W.L. et al., "Nutritional modulation of neonatal outcomes", AACN Clinical Issues, (2004), 15(1), 83-96.
Kuwata, H. et al., "Functional Fragments of ingested lactoferrin are resistant to proteolytic degradation in the gastrointestinal tract of adults rats", J. Nutr., (2001), 131, 2121-2127.
Ronayne De Ferrer, P.A., et al., "Lactoferrin levels in term and preterm milk", J. Am. Coll. Nutr., (2000), 19(3), 370-373.
Satue-Gracia, M. T., et al., "Lactoferrin in infant formulas: effect on oxidation", J. Agric. Food Chem., (2000), 48, 4984-4990.
Tani, F., et al., "Isolation and characterization of opioid antagonist peptides derived from human lactoferrin", Agric. Biol. Chem., (1990), 54(7), 1803-1810.
Zisman, D.A., et al., "MCP-1 protects mice in lethal endotoxemia", J. Clin. Invest. (1997) 99(12), 2832-2836.

* cited by examiner

*Primary Examiner* — Cecilia J Tsang
*Assistant Examiner* — Randall L Beane
(74) *Attorney, Agent, or Firm* — Carol Miernicki Steeg

(57) ABSTRACT

The present invention provides for novel peptides derived from human milk. In aspects of the invention, the peptides are capable, individually or in combination, of evoking an anti-oxidative stress response, immunomodulation, anti-inflammatory response and anti-pathogenic response. As such the peptides of the invention may be used in food supplements, milk substitutions, infant formula., mother's milk, parenteral nutrition solutions, cell/tissue/organ storage and perfusion solutions and pharmaceutical formulations.

18 Claims, 15 Drawing Sheets

SEQUENCE LISTING

<160> NUMBER OF SEQ ID NOS: 37

<210> SEQ ID NO 1
<211> LENGTH: 5
<212> TYPE: PRT
<213> ORGANISM: Homo sapiens

<400> SEQUENCE: 1

Val Pro Val Gln Ala
1               5

<210> SEQ ID NO 2
<211> LENGTH: 5
<212> TYPE: PRT
<213> ORGANISM: Homo sapiens

<400> SEQUENCE: 2

Val Pro Tyr Pro Gln
1               5

<210> SEQ ID NO 3
<211> LENGTH: 7
<212> TYPE: PRT
<213> ORGANISM: Homo sapiens

<400> SEQUENCE: 3

Leu Leu Asn Pro Thr His Gln
1               5

<210> SEQ ID NO 4
<211> LENGTH: 10
<212> TYPE: PRT
<213> ORGANISM: Homo sapiens

<400> SEQUENCE: 4

Leu Glu Asn Leu His Leu Pro Leu Pro Leu
1               5                   10

<210> SEQ ID NO 5
<211> LENGTH: 11
<212> TYPE: PRT
<213> ORGANISM: Homo sapiens

<400> SEQUENCE: 5

Asp Leu Glu Asn Leu His Leu Pro Leu Pro Leu
1               5                   10

<210> SEQ ID NO 6
<211> LENGTH: 12
<212> TYPE: PRT
<213> ORGANISM: Homo sapiens

<400> SEQUENCE: 6

Thr Asp Leu Glu Asn Leu His Leu Pro Leu Pro Leu
1               5                   10

<210> SEQ ID NO 7
<211> LENGTH: 20
<212> TYPE: PRT
<213> ORGANISM: Homo sapiens

<400> SEQUENCE: 7

Val Lys His Glu Asp Gln Gln Gln Gly Glu Asp Glu His Gln Asp Lys
1               5                   10                  15

```
Ile Tyr Pro Ser
           20

<210> SEQ ID NO 8
<211> LENGTH: 6
<212> TYPE: PRT
<213> ORGANISM: Homo sapiens

<400> SEQUENCE: 8

Val Pro Asn Ser Tyr Pro
1               5

<210> SEQ ID NO 9
<211> LENGTH: 6
<212> TYPE: PRT
<213> ORGANISM: Homo sapiens

<400> SEQUENCE: 9

Asn Pro Tyr Val Pro Arg
1               5

<210> SEQ ID NO 10
<211> LENGTH: 7
<212> TYPE: PRT
<213> ORGANISM: Homo sapiens

<400> SEQUENCE: 10

Asn Asn Pro Tyr Val Pro Arg
1               5

<210> SEQ ID NO 11
<211> LENGTH: 11
<212> TYPE: PRT
<213> ORGANISM: Homo sapiens

<400> SEQUENCE: 11

Ala Glu Asn Pro Glu Gly Glu Lys Glu Ala
1               5                   10

<210> SEQ ID NO 12
<211> LENGTH: 10
<212> TYPE: PRT
<213> ORGANISM: Homo sapiens

<400> SEQUENCE: 12

Pro Pro Phe Ser Asp Ile Ser Asn Pro Thr
1               5                   10

<210> SEQ ID NO 13
<211> LENGTH: 13
<212> TYPE: PRT
<213> ORGANISM: Homo sapiens

<400> SEQUENCE: 13

Leu Leu Cys Asn Leu Glu Leu His Asn Ser Pro Ser Gly
1               5                   10

<210> SEQ ID NO 14
<211> LENGTH: 10
<212> TYPE: PRT
<213> ORGANISM: Homo sapiens

<400> SEQUENCE: 14

Gly Glu Ile Thr Ser Arg Ala Ala Val Asp
1               5                   10
```

<210> SEQ ID NO 15
<211> LENGTH: 10
<212> TYPE: PRT
<213> ORGANISM: Homo sapiens

<400> SEQUENCE: 15

Phe Ala Ala Ala Ser Ile Gly Gln Val His
1               5                   10

<210> SEQ ID NO 16
<211> LENGTH: 7
<212> TYPE: PRT
<213> ORGANISM: Homo sapiens

<400> SEQUENCE: 16

Val Asn Pro Tyr Ser His Lys
1               5

<210> SEQ ID NO 17
<211> LENGTH: 26
<212> TYPE: PRT
<213> ORGANISM: Homo sapiens

<400> SEQUENCE: 17

Pro Cys Gly Ile Ala Gly Pro Gly Ile Gly Trp Glu Gln Asp Pro
1               5                   10                  15

Asp Ser Cys Arg Arg Asn Gly Ser Cys Arg
                20                  25

<210> SEQ ID NO 18
<211> LENGTH: 11
<212> TYPE: PRT
<213> ORGANISM: Homo sapiens

<400> SEQUENCE: 18

Asn Leu Leu Gly Gly Gly Ser Leu Pro Thr Pro
1               5                   10

<210> SEQ ID NO 19
<211> LENGTH: 6
<212> TYPE: PRT
<213> ORGANISM: Homo sapiens

<400> SEQUENCE: 19

Tyr Gly Tyr Thr Gly Ala
1               5

<210> SEQ ID NO 20
<211> LENGTH: 11
<212> TYPE: PRT
<213> ORGANISM: Homo sapiens

<400> SEQUENCE: 20

Gly Pro Ala Gly Leu Pro Gly Ile Gly Ala Val
1               5                   10

<210> SEQ ID NO 21
<211> LENGTH: 9
<212> TYPE: PRT
<213> ORGANISM: Homo sapiens

<400> SEQUENCE: 21

Val Asn Glu Glu Ser Thr Ile Pro Arg
1               5

```
<210> SEQ ID NO 22
<211> LENGTH: 6
<212> TYPE: PRT
<213> ORGANISM: Homo sapiens

<400> SEQUENCE: 22

Ile Ser Glu Leu Gly Trp
1               5

<210> SEQ ID NO 23
<211> LENGTH: 8
<212> TYPE: PRT
<213> ORGANISM: Homo sapiens

<400> SEQUENCE: 23

His Val Tyr Phe Cys Ala Lys Glu
1               5

<210> SEQ ID NO 24
<211> LENGTH: 10
<212> TYPE: PRT
<213> ORGANISM: Homo sapiens

<400> SEQUENCE: 24

Asp Pro Ala Val Ser Cys Lys Cys Val Gly
1               5                   10

<210> SEQ ID NO 25
<211> LENGTH: 11
<212> TYPE: PRT
<213> ORGANISM: Homo sapiens

<400> SEQUENCE: 25

Val Val Ala Pro Glu Ala Ala Gln Thr Arg Val
1               5                   10

<210> SEQ ID NO 26
<211> LENGTH: 15
<212> TYPE: PRT
<213> ORGANISM: Homo sapiens

<400> SEQUENCE: 26

Phe Pro Pro Asp Val Thr Gly Asn Leu Asp Tyr Lys Asn Lys Val
1               5                   10                  15

<210> SEQ ID NO 27
<211> LENGTH: 16
<212> TYPE: PRT
<213> ORGANISM: Homo sapiens

<400> SEQUENCE: 27

His Ala Ser Thr Ala Lys Ser Pro Ser Thr Glu Thr Leu Asp Arg Gln
1               5                   10                  15

<210> SEQ ID NO 28
<211> LENGTH: 4
<212> TYPE: PRT
<213> ORGANISM: Homo sapiens

<400> SEQUENCE: 28

His Asn Pro Ile
1

<210> SEQ ID NO 29
```

```
<211> LENGTH: 6
<212> TYPE: PRT
<213> ORGANISM: Homo sapiens

<400> SEQUENCE: 29

Pro Leu Ala Gln Pro Ala
1               5

<210> SEQ ID NO 30
<211> LENGTH: 6
<212> TYPE: PRT
<213> ORGANISM: Artificial Sequence
<220> FEATURE:
<223> OTHER INFORMATION: Synthesized

<400> SEQUENCE: 30

Trp Ile Ser Glu Leu Gly
1               5

<210> SEQ ID NO 31
<211> LENGTH: 7
<212> TYPE: PRT
<213> ORGANISM: Artificial Sequence
<220> FEATURE:
<223> OTHER INFORMATION: Synthesized

<400> SEQUENCE: 31

Trp Ile Ser Glu Leu Gly Trp
1               5

<210> SEQ ID NO 32
<211> LENGTH: 6
<212> TYPE: PRT
<213> ORGANISM: Artificial Sequence
<220> FEATURE:
<223> OTHER INFORMATION: Synthesized

<400> SEQUENCE: 32

Ile Ser Glu Leu Trp Gly
1               5

<210> SEQ ID NO 33
<211> LENGTH: 6
<212> TYPE: PRT
<213> ORGANISM: Artificial Sequence
<220> FEATURE:
<223> OTHER INFORMATION: Synthesized

<400> SEQUENCE: 33

Ile Ser Glu Leu Gly Phe
1               5

<210> SEQ ID NO 34
<211> LENGTH: 6
<212> TYPE: PRT
<213> ORGANISM: Artificial Sequence
<220> FEATURE:
<223> OTHER INFORMATION: Synthesized

<400> SEQUENCE: 34

Ile Ser Glu Leu Gly Tyr
1               5

<210> SEQ ID NO 35
<211> LENGTH: 6
<212> TYPE: PRT
<213> ORGANISM: Artificial Sequence
<220> FEATURE:
```

```
<223> OTHER INFORMATION: Synthesized
<220> FEATURE:
<221> NAME/KEY: MOD_RES
<222> LOCATION: (1)..(1)
<223> OTHER INFORMATION: Ac-Ile

<400> SEQUENCE: 35

Xaa Ser Glu Leu Gly Trp
1               5

<210> SEQ ID NO 36
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (6)..(6)
<223> OTHER INFORMATION: Trp-NH2

<400> SEQUENCE: 36

Ile Ser Glu Leu Gly Xaa
1               5

<210> SEQ ID NO 37
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (2)..(2)
<223> OTHER INFORMATION: Phospho-Ser

<400> SEQUENCE: 37

Ile Xaa Glu Leu Gly Trp
1               5
```

HUMAN MILK PEPTIDES

FIELD OF THE INVENTION

The present invention relates to novel peptides and their use in the manufacture of compositions having antioxidant, anti-inflammatory, immunomodulatory and antipathogenic properties, and in methods of treatment of disorders that result From oxidative stress, inflammation and pathogens. Specifically the present invention relates to novel peptides that are derived from human milk.

BACKGROUND OF THE INVENTION

Throughout this application, various references are cited in square brackets to describe more fully the state of the art to which this invention pertains. Full bibliographic information for each citation is found at the end of the specification, immediately preceding the claims. The disclosure of the references is hereby incorporated by reference into the present disclosure.

Oxidative stress (OS) is a biological state that occurs when a cell's antioxidant capacity is overwhelmed by reactive oxygen species (ROS), causing a redox imbalance. ROS are a type of free radical, which is formed with oxygen. Free radicals are chemical substances that contain one or more unpaired orbital electrons and are therefore unstable and liable to react with other molecules to form more stable compounds with a lower energy state. In an attempt to achieve this stable state, ROS reacts with proteins, lipids, and DNA, This can result in damage and even inactivation of cellular components such as enzymes, membranes, and DNA. As such, ROS and oxidative stress as a whole have been suggested to participate in the initiation and/or propagation of diseases such as cardiovascular and inflammatory diseases, cancer, and diabetes [Valko M. et al. Mol. Cell. Biochem. 266(1-2)37 (2004)].

ROS can be produced on a regular basis during oxidative metabolism and in more potent levels during inflammation [Rosen G M, et al. FASEB J. 9(2):200 (1995)]. Therefore, antioxidative stress mechanisms and antioxidants are key to limiting the proliferation of ROS and re-establishing a stable redox balance.

It is generally known that antioxidants are required in a certain minimum amount to maintain infant health. Premature infants (<1500 g birthweight) are subject to diseases as a result of oxidative stress [Saugstadt O D. Acta Pediatr Scand. 79: 881 (1990)]. A number of beneficial effects have been ascribed to human breast milk [Diehl-Jones W L and Askin D F. American Association of Critical Care Nurses (AACN) Clin Issues 15: 83 (2004)]. Infants fed with human milk are found to gain protection against necrotizing enterocolitis, and have fewer upper respiratory tract infections and systemic infections.

Given the challenges for maintaining human milk supplies, mother milk substitutes, such as infant formula or other animal's milk may be the only option for many infants.

There is, therefore, a need for new compounds derived from mother's milk that provide antioxidant advantages and may be used as ingredients to mothers' milk substitutes.

SUMMARY OF THE INVENTION

The present invention relates to the discovery of 27 novel peptides derived from human milk (SEQ ID NOs. 1 to 27).

Thus in one aspect, the present invention provides for an isolated peptide comprising a sequence selected from the group consisting of SEQ ID NO. 1 to SEQ ID NO. 27 and SEQ ID NO. 30 to SEQ ID NO. 37.

In another aspect, the present invention provides for an isolated DNA and a vector comprising said DNA, said DNA comprising a sequence encoding amino acids according to SEQ. ID No. 1 to SEQ ID NO. 27 and SEQ. ID No. 30 to SEQ 1D NO. 34.

The present invention also relates to the discovery of peptides derived from human milk, wherein said peptides are capable of eliciting one or more of the following responses: antioxidative, anti-inflammatory, immunomodulation and antipathogenic.

Thus, according to one aspect, the present invention provides for a peptide, said peptide comprises at least one of the amino acid sequences selected from the group consisting of SEQ ID NO. 1 to SEQ ID NO. 37wherein said peptide is capable of eliciting at least one of the following responses: antioxidative, immunomodulation, anti-inflammatory and anti-pathogenic.

According to another aspect, the present invention provides for a peptide having antioxidant. properties, said peptide comprising at least one of the amino acid sequences selected from the group consisting of SEQ ID NOs. 1, 2, 8, 9, 19, 22, 28 to 37. In aspects of the invention, the peptides of the invention may have tyrosine and tryptophan residues added to the peptides to increase their antioxidant properties.

According to yet another aspect, the present invention provides for one or more peptides comprising an amino acid sequence selected from the group of amino acid sequences consisting of SEQ ID NO. 1 to SEQ ID NO. 37 wherein said peptides may be used in the manufacture of a composition, wherein said composition is capable of inducing at least one of the following responses: antioxidative, immunomodulation, anti-inflammatory and anti-pathogen.

According to another aspect, the present invention provides for the manufacture or compositions selected from the group comprising of food, food supplements, food solution supplements, pharmaceutical compositions, milk substitutions, infant formula, mother's milk, total/partial nutritional solutions, storage/perfusion solutions and pharmaceutical formulations.

According to another aspect yet, the present invention provides for a pharmaceutical composition comprising an effective amount of one or more of the peptides of SEQ ID NOs. 1 to 37, and a pharmaceutically acceptable carrier, wherein said pharmaceutical composition is useful in the treatment of a condition resulting from oxidative stress.

According to a further aspect, the present invention provides for an antiinflammatory pharmaceutical composition comprising an effective amount of one or more of the peptides of SEQ ID NOs. 1 to 37, and a pharmaceutically acceptable carrier.

According to yet a further aspect, the present invention provides for a pharmaceutical composition useful in the treatment of a pathogenic infection, wherein said composition comprises an effective amount of one or more of the peptides of SEQ ID NOs. 1 to 37, and a pharmaceutically acceptable carrier.

The pharmaceutical compositions of the present invention may additionally comprise an adjuvant.

According to a further aspect yet of the present invention, there is provided a composition having antioxidant properties, wherein said composition comprises one or more peptides selected from the group consisting of: SEQ ID NOs. 1, 2, 8, 9, 19, 22, 28 to 37.

According to one aspect, the present invention provides for a method for treating a subject suffering from an oxidative stress condition, said method comprising administering an effective amount a composition comprising one or more peptides having antioxidant properties, wherein said one or more peptides are selected from the group comprising of SEQ ID NO. 1 to SEQ ID NO. 37.

According to another aspect, the present invention provides for a method for treating a subject suffering from an oxidative stress condition, said method comprising administering an effective amount a composition having antioxidant properties, said composition comprising one or more peptides, wherein said one or more peptides are selected from the group consisting of: SEQ ID NOs. 1, 2, 8, 9, 19, 22, 28 to 37.

According to yet another aspect, the present invention provides for a method for treating an inflammatory reaction in a subject, said method comprising administering an effective amount a composition comprising one or more peptides, wherein said one or more peptides are selected from the group comprising of SEQ ID NO. 1 to SEQ ID NO. 37.

According to another aspect yet, the present invention provides for a method for treating a subject against a pathogenic infection, said method comprising administering an effective amount a composition comprising one or more peptides, wherein said one or more peptides are selected from the group comprising of SEQ ID NO. 1 to SEQ ID NO. 37.

According to another aspect, the invention provides for a peptide selected from the group comprising of SEQ ID NO. 1 to SEQ ID NO. 37 and its use in methods and compositions to alter the immune system in a subject.

According to a further aspect, the present invention provides For a method for supplementing a diet of a neonate subject, comprising administering as part of the diet an effective amount of a supplement comprising an effective amount of one or more peptide having antioxidant properties, wherein said at least one peptide is selected from the group consisting of: SEQ ID NOs. 1, 2, 8, 9, 19, 22, 28 to 37.

According to yet a further aspect, the present invention provides for an improved Parenteral Nutrition (PN) solution, wherein said PN solution comprises one or more peptides, wherein said peptides are selected from the group comprising of SEQ ID NOs. 1 to 37, and wherein said peptides operate to prevent photo-oxidation of PN components.

According to yet a further aspect, the present invention provides for addition of peptides into a solution to prevent photooxidation of the components of the solution, in which the peptides comprise one or more peptides, wherein said one or more peptides are selected from the group comprising of SEQ ID NOs. 1 to 37.

According to a further aspect yet, the present invention provides for a composition for maintaining cells, tissues and/or organs in a viable state ex vivo during storage and in vivo during perfusion, wherein said composition comprises one or more peptides, wherein said peptides are selected From the group comprising of SEQ ID NOs. 1 to 37.

In one aspect, the present invention provides for an antibody raised against a peptide, wherein said peptide comprises an amino acid sequence selected from the group consisting of SEQ ID NO. 1 to SEQ ID NO. 37.

In aspects of the invention, the peptides of the invention are derived from human milk.

In aspects of the invention, the peptides of the invention may have added: cysteines to one or both ends of the peptide to circularize by means of disulfide bond formation, phosphorous groups and acetyl groups.

Also within the scope of the invention are functional analogues of any of the peptides of the invention as well as multimers of the peptides according to the invention such as for example a dimer or trimer of the peptides according to the invention. A multimer according to the invention can either be a homomer, consisting of a multitude of the same peptide, or a heteromer consisting of different peptides. The characteristic amino acid sequences of the peptides according to the invention can be flanked by random amino acid sequences. Preferred are flanking sequences that have a stabilizing effect on the peptides, thus increasing their biological availability.

Also within the scope of the invention are peptides characterized by at least one amino acid being replaced by another amino acid with similar chemical properties; at least one additional amino acid being present at the N-or/and C-terminus; at least one amino acid being deleted; and at least one amino acid being chemically modified.

Advantages of the present invention include the discovery of novel peptides derived from human mothers' milk that can be added to an infant's diet and ameliorate diseases that are caused by oxidative stress, inflammation and pathogens. Nine of the novel amino acid of the present invention are released from human beta-casein and three from human kappa-casein. The amino acid sequences of beta-casein and kappa-casein proteins differ between human and cow's milk. Therefore, the neonatal digestion of mother's milk substitutes, such as infant formula or other animals' milk, cannot yield the peptides described herein.

Other features and advantages of the present invention will become apparent from the following detailed description. It should be understood, however, that the detailed description and the specific examples while indicating embodiments of the invention arc given by way of illustration only, since various changes and modifications within the spirit and scope of the invention will become apparent to those skilled in the art from said detailed description.

BRIEF DESCRIPTION OF THE DRAWINGS

The present invention will become more fully understood from the detailed description given herein and from the accompanying drawings, which are given by way of illustration only and do not limit the intended scope of the invention.

DETAILED DESCRIPTION OF THE INVENTION

In one aspect, the present invention provides for an isolated peptide comprising a sequence selected from the group consisting of SEQ ID NO. 1 to SEQ ID NO. 27 and SEQ ID NO. 30 to SEQ ID NO. 37.

In one aspect, the present invention provides for a peptide, said peptide comprising at least one of the amino acid sequences selected from the group consisting of SEQ ID NO. 1 to SEQ ID NO. 37, wherein said peptide is capable of inducing at least one of the following responses: antioxidative, immunomodulation, anti-inflammatory or anti-pathogenic.

According to another aspect, the instant invention provides for peptides having antioxidant properties. Thus, according to another aspect, the present invention provides for a peptide having antioxidant properties, said peptide comprising at least one of the amino acid sequences selected from the group consisting of SEQ ID NOs. 1, 2, 8, 9, 19, 22, 28 to 37.

A number of beneficial effects have been ascribed to human breast milk (Diehl-Jones & Askin, 2004). Accordingly, the Applicant's research has been directed at: (i) identifying specific milk peptides in biologically-active fractions of digested milk; (ii) determining the biological activity of said peptides; and (iii) determining derivitives of said peptides with biological activity.

Figure 1:
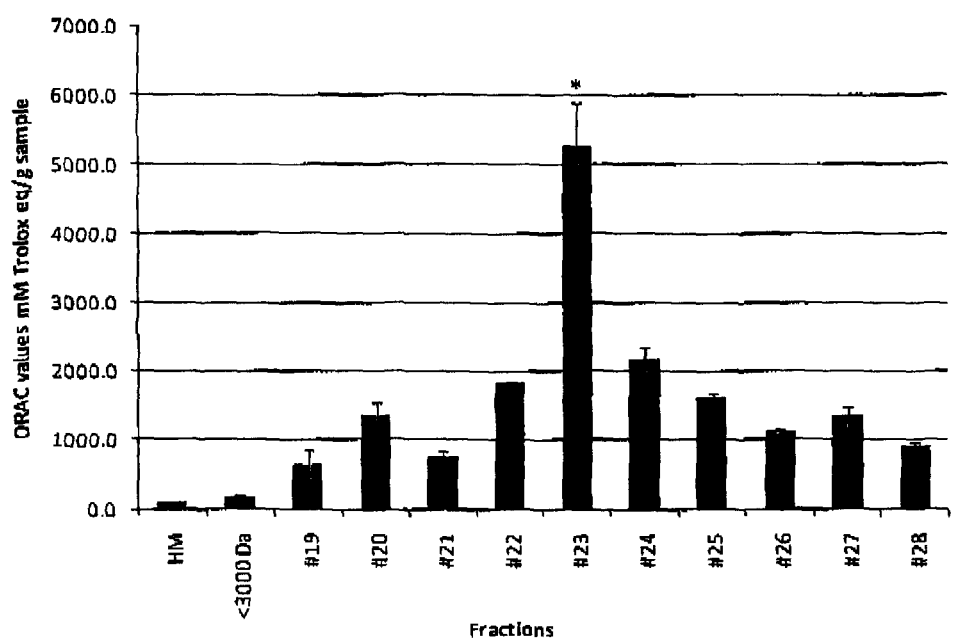
FIG. 1 illustrates oxygen radical absorbance capacity (hereinafter "ORAC") values of peptide fractions ($\leqq 3000$ Da) from preparative high performance liquid chromatography (HPLC). The results are expressed as Trolox equivalents per gram of sample.

Using a method that simulates the gastric and intestinal digestion of a premature infant, the Applicant has identified a set of peptides within the human mother's milk capable of scavenging peroxyl radicals. As illustrated in FIG. 1, using the Oxygen Radical Absorbance Capacity (ORAC) of High Performance Liquid Chromatography (HPLC) fractions obtained from the digested mother's milk, the Applicant discovered that fraction No. 23 provided the highest ORAC value (5274 ±630 μM Trolox eq/g sample), which is, surprisingly, about 65 times higher than the ORAC value for whole human milk sample.

As provided in the Examples, the Applicant identified the peptides in fraction No. 23, which are listed in the Sequencing Listing as SEQ ID NOs. 1 to 29.

Taken together, the present invention demonstrates a set of peptides that in aspects are derived from beta-casein, kappa-casein and other milk proteins amino acid sequences and in other aspects based on artificial peptide sequences. The term "peptide" as used herein is defined as a chain of amino acid residues, usually having a defined sequence. As used herein the term peptide is mutually inclusive of the terms "peptides" and "proteins".

The peptides of the present invention may be modified by the addition cysteine residues to one or both ends of the peptides to circularize the peptides by the formation of disulfide bond formation. The peptides of the present invention may be modified by the addition of phosphorus and acetyls groups. Phosphorylation is one of the most common protein modifications that occur in animal cells [Guo, Yan-Ting et al. International Journal of Peptide Research and Therapeutics 11:159 (2005)]. It occurs most commonly on threonine, serine and tyrosine residues and plays critical roles in the regulation of many cellular processes including: cell cycle, growth, apoptosis and differentiation [Guo, Yan-Ting at al. International Journal of Peptide Research and Therapeutics 11:159 (2005)]. This procedure is possible because some of the peptides of the present invention contain tyrosine and because an acyl group can be added to N-terminal amino acid [Aniel A. et al. Rapid Comm Mass Spectr. 21:2237 (2007)]. The two amino acids tryptophan and tyrosine in the peptides of the invention may be substituted with other amino acids to evaluate their effects on peptide activities.

The peptides of the invention may be of about at least 4 amino acids in length and about 4 to about 26 amino acids in length and include any ranges of length therein (i.e 4-26, 4-20, 4-15, etc.) as is understood by one of skill in the art. Peptides of over about 26 amino acids in length are also encompassed by the present invention. The length of peptide being only restricted by its ability to induce at least one of the following responses: antioxidative, immunomodulation, anti-inflammatory or anti-pathogenic. The peptides of the invention may also include dimers and trimers of the peptides as well as additional stabilizing flanking sequences as is understood by those of skill in the art and described for example in U.S. Pat. Nos. 5,824,315 and 6,184,204 (the disclosures of which are incorporated herein by reference in their entirety). A multimer according to the invention can either be a homomer, consisting of a multitude of the same peptide, or a heteromer consisting of different peptides. As stated, the amino acid sequences of the peptides according to the invention can be flanked by random amino acid sequences. Preferred are flanking sequences that have a stabilizing effect on the peptides, thus increasing their biological availability. In addition, other peptidomimetics are also useful in the peptides of the present invention. The peptides of the invention also encompass peptides that have been modified by, for example, phosphorylation, glycosylation or lipidation. Furthermore, the peptides of the present invention may also encompass "functionally equivalent variants" or "analogues" of the peptides. As such, this would include but not be limited to peptides and polypeptides with partial sequence homology, peptides having one or more specific conservative and/or non-conservative amino acid changes and peptide conjugates which do not alter the biological or structural properties of the peptide (i.e. the ability to induce at least one of the following responses: antioxidative, immunomodulation, anti-inflammatory or anti-pathogenic).

In terms of "functional analogues", it is well understood by those skilled in the art, that inherent in the definition of a biologically functional peptide analogue is the concept that there is a limit to the number of changes that may be made within a defined portion of the molecule and still result in a molecule with an acceptable level of equivalent biological activity, which, in this case, would include the ability to induce at least one of the following responses: antioxidative, immunomodulation, anti-inflammatory or anti-pathogenic. A plurality of distinct peptides/proteins with different substitutions may easily be made and used in accordance with the invention. It is also understood that certain residues are particularly important to the biological or structural properties of a protein or peptide such as residues in the receptor recognition region, such residues of which may not generally be exchanged.

As such, the Applicant has also tested 8 derivitives of SEQ ID NO. 22 (SEQ ID NO. 30 to SEQ ID NO. 37).

Functional analogues can be generated by conservative or non-conservative amino acid substitutions. Amino acid substitutions are generally based on the relative similarity of the amino acid side-chain substituents, for example, their hydrophobicity, hydrophilicity, charge, size and the like. Thus, within the scope of the invention, conservative amino acid changes means, an amino acid change at a particular position which is of the same type as originally present; i.e. a hydrophobic amino acid exchanged for a hydrophobic amino acid, a basic amino acid for a basic amino acid, etc. Examples of conservative substitutions include the substitution of non-polar (hydrophobic) residues such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes result in functional analogues in that they do not significantly alter the overall charge and/or configuration of the peptide. Examples of such conservative changes are well-known to the skilled artisan and are within the scope of the present invention. Conservative substitution also includes the use of a chemically derivatized residue in place of a non-derivatized residue provided that the resulting peptide is a biologically functional equivalent to the peptides of the invention. Therefore, the peptides of the present invention encompass a peptide having an amino acid sequence that differs from SEQ ID Nos. 1-29.

The peptides of the invention also encompass a peptide having an amino acid sequence that differs from SEQ ID Nos. 1-29 by a single mutation, where the single mutation represents a single amino acid deletion, insertion or substitution.

The peptides of the invention may be further isolated and purified from human milk by methods selected on the basis of properties revealed by its sequence. Purification can be achieved by protein purification procedures such as chromatography methods (gel-filtration, ion-exchange and immunoaffinity), by high-performance liquid chromatography (HPLC, RP-HPLC, ion-exchange HPLC, size-exclusion HPLC, high-performance chromato focusing and hydrophobic interaction chomatography) or by precipitation (immunoprecipitation). Polyacrylamide gel electrophoresis can also be used to isolate the proteins based on the molecular weight of the protein, charge properties and hydrophobicity. The purified proteins can be used in further biochemical analyses to establish secondary and tertiary structure which may aid in the design of pharmaceuticals to interact with the protein, alter the protein charge configuration or charge interaction with other proteins or alter its function.

The peptides of the present invention may be made by methods known to those of skill in the art most notably and preferably by chemical synthesis using techniques well known in the chemistry of proteins such as solid phase synthesis [J. Am. Chem. Assoc. 65:2149 (1964); J. Amer. Chem. Soc. 85:2149 (1963); and Int. J. Peptide Protein Res. 35:161-214 (1990)] or synthesis in homogenous solution [Methods of Organic Chemistry, E. Wansch (Ed.) Vol. 15, pts. I and II, Thieme, Stuttgart (1987)] to generate synthetic peptides.

Alternatively, the peptides of the invention may be made by the use of recombinant DNA techniques known to one skilled in the art.

It is further contemplated that the invention encompasses vectors which comprise nucleic acids coding for at least one of the peptides of the present invention.

An embodiment of the present invention further encompasses compositions having antioxidant, anti-inflammatory, immunomodulatory and antipathogenic properties. Thus, according to a further aspect, the present invention provides for one or more peptides comprising an amino acid sequence selected from the group of amino acid sequences consisting of SEQ ID NO. 1 to SEQ ID NO. 37 wherein said peptides may be used in the manufacture of a composition, wherein said composition is capable of inducing at least one of the following responses: antioxidant, immunomodulation, anti-inflammatory or anti-pathogen.

In another embodiment, the peptides of the present invention can be used in the manufacture of a composition which may be selected from the group comprising of: food supplements, food solution supplements, nutraceutical compositions, pharmaceutical compositions, milk substitutions, infant formula, mother's milk, total/partial nutritional solutions, storage/reperfusion solutions and pharmaceutical formulations.

According to an embodiment of the invention, a food can include any solid or liquid food product.

According to an embodiment of the invention, a food solution can include but is not limited to soft drinks, milk, juices, and other liquid food products.

According to an embodiment of the invention, a nutraceutical composition is defined as a product that maintains basic physiological, biological, and metabolic functions within an animal, including but not limited to humans.

In aspects, the compositions of the invention comprise one or more peptides of the invention for administration to subjects in a biologically compatible form suitable for administration in vivo.

By "biologically compatible form suitable for administration in vivo" is meant a form of the substance to be administered in which any toxic effects are outweighed by the therapeutic effects. The substances may be administered to any animal, preferably, humans. Administration of a therapeutically active amount of the pharmaceutical compositions of the present invention, or an "effective amount", is defined as an amount effective at dosages and for periods of time, necessary to achieve the desired result of eliciting an immune response in a human. Suitable administration routes are intramuscular injections, subcutaneous injections, intravenous injections or intraperitoneal injections, oral and intranasal administration.

Acceptable carriers are well known to those skilled in the art and include, for example, sterile saline, lactose, sucrose, calcium phosphate, gelatin, dextrin, agar, pectin, peanut oil, olive oil, sesame oil and deionised water.

Furthermore the composition according to the invention may comprise one or more stabilizers such as, for example, carbohydrates including sorbitol, mannitol, starch, sucrose, dextrin and glucose, proteins such as albumin or casein, and buffers like alkaline phosphates. Furthermore, the composition of the present invention may comprise one or more adjuvants that enhance the antioxidative properties of the peptides of the invention.

Figure 4:
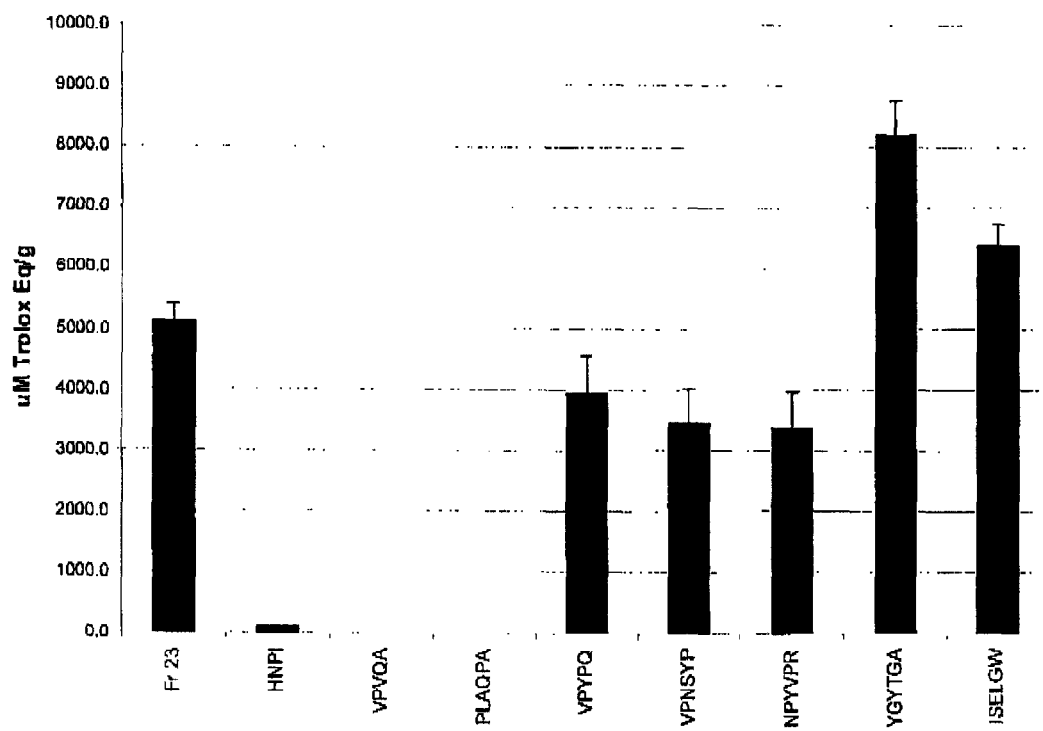
FIG. 4 illustrates ORAL values of Fraction #23 and synthetic peptides identified using MS/MS analysis in this fraction. Results are expressed as Mean ±SD.
Figure 5:
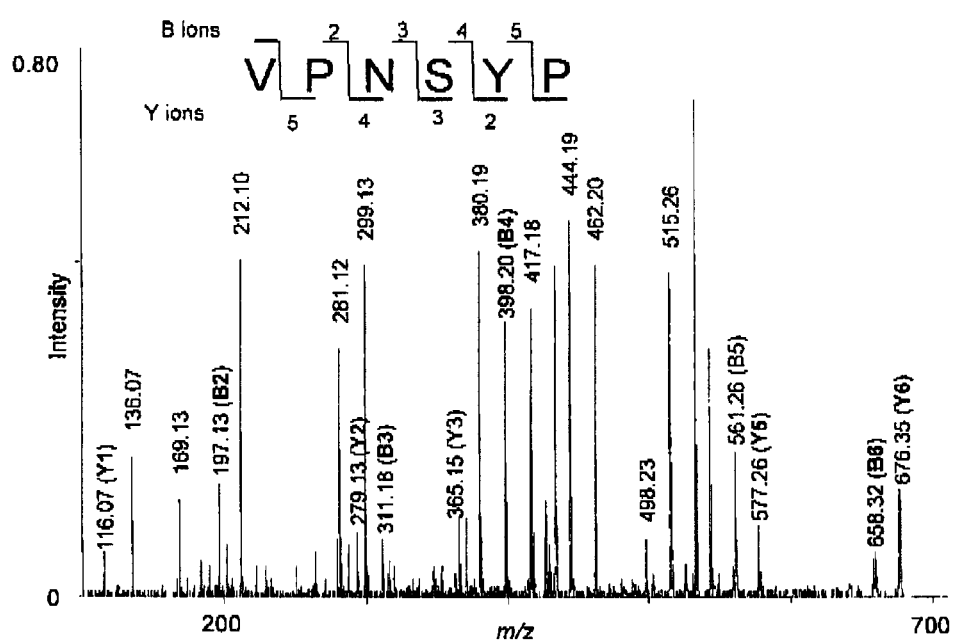
FIG. 5 illustrates MS/MS spectrum of ion m/z 676.35 (SEQ ID NO. 8), following sequence interpretation database searching the sequence was match to kappa-casein f(31-36).
Figure 6:
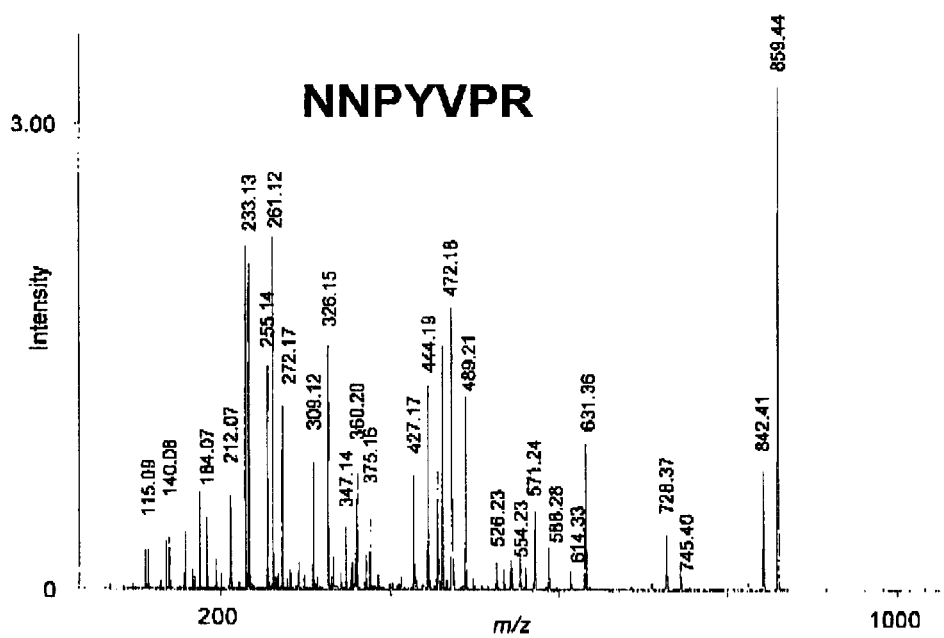
FIG. 6 illustrates MS/MS spectrum of ion m/z 859.4 (SEQ ID NO. 10), following sequence interpretation database searching the sequence was match to kappa-casein f(52-58).
Figure 7:
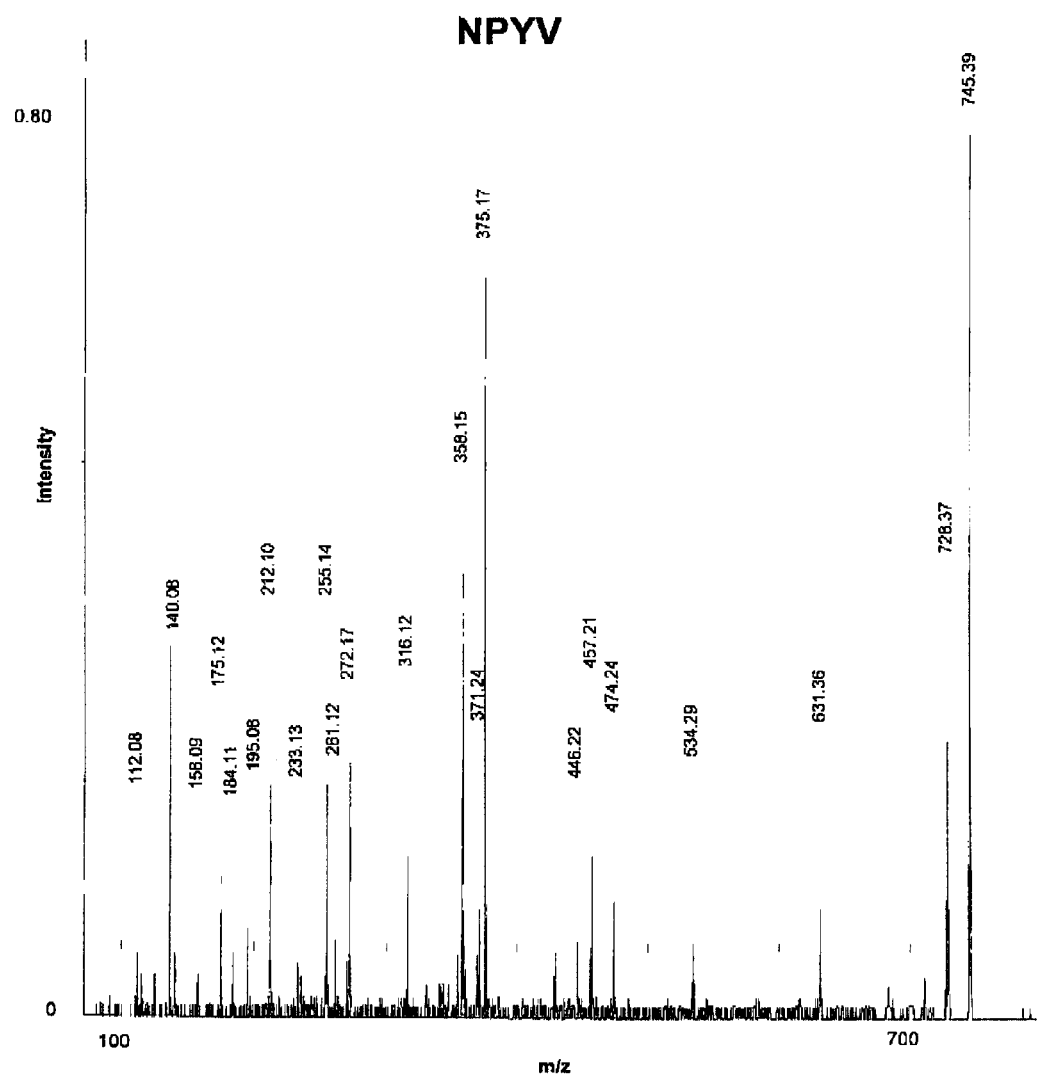
FIG. 7 illustrates MS/MS spectrum of ion m/z 745.4 (SEQ ID NO. 9) following sequence interpretation database searching the sequence was match to kappa-casein f(53-58).
Figure 8:
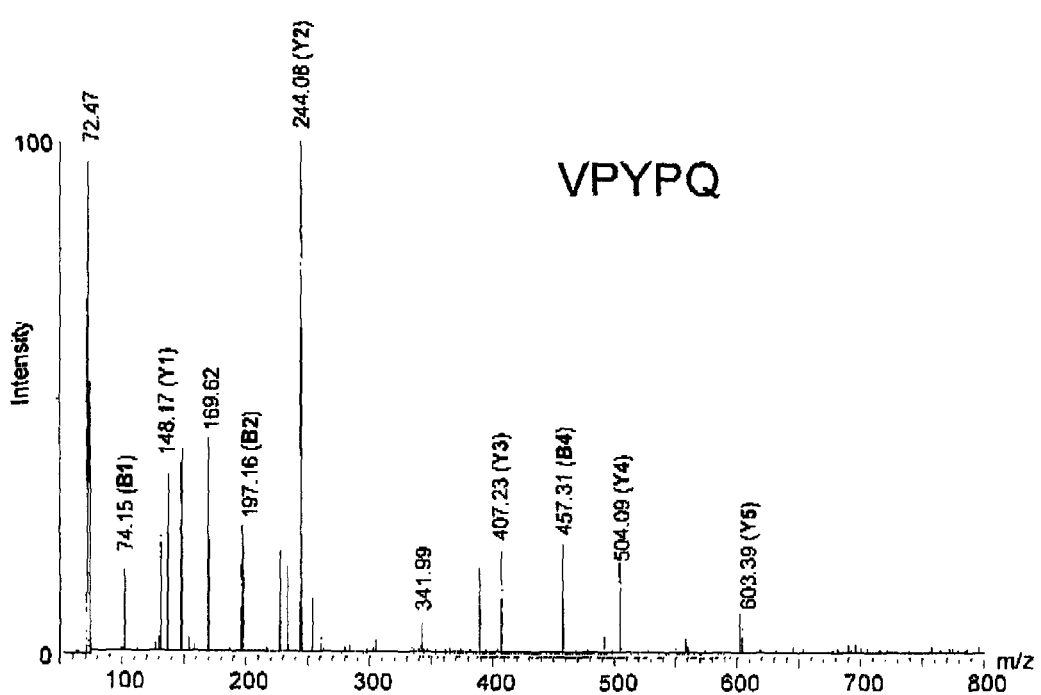
FIG. 8 illustrates MS/MS spectrum of ion m/z 603.39 (SEQ ID NO. 2), following sequence interpretation database searching the sequence was match to beta-casein f(169-173).
Figure 9:
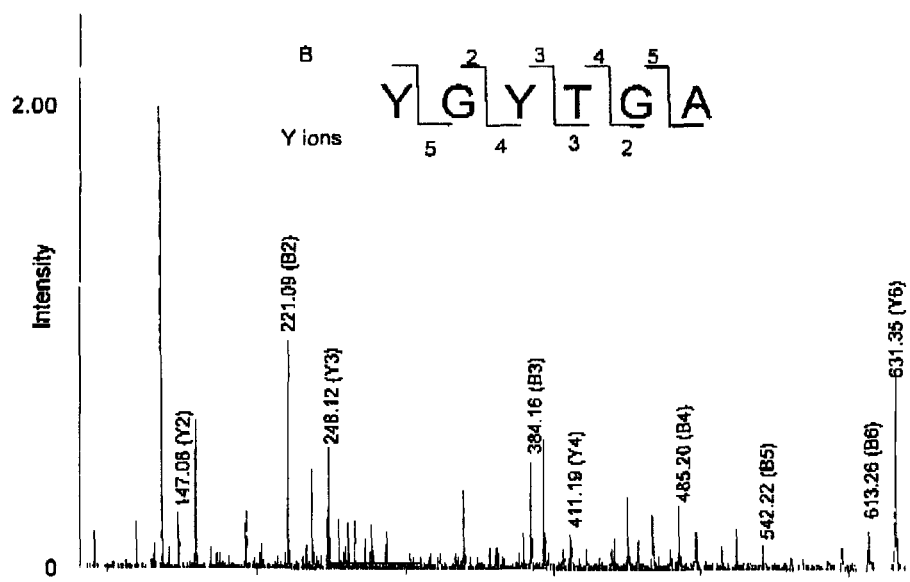
FIG. 9 illustrates MS/MS spectrum of ion m/z 631.3 (SEQ ID NO. 19), following sequence interpretation database searching the sequence was not match to a human milk protein.
Figure 10:
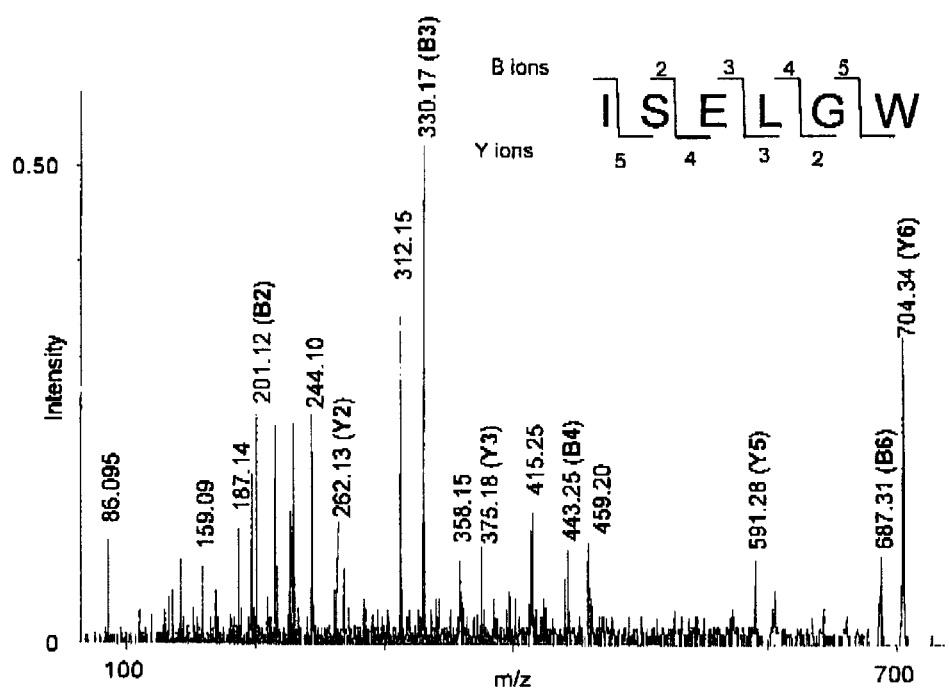
FIG. 10 illustrates MS/MS spectrum of ion m/z 704.3 (SEQ ID NO. 22), following sequence interpretation database searching the sequence was not match to a human milk protein.

As illustrated in FIG. 4, using an ORAC analysis, for the first time, specific peptides derived from human mother's milk having antioxidant properties were identified. Peptides of SEQ ID NOs 19 and 22 showed the most radical scavenging properties. Peptide of SEQ ID NO. 19 includes the amino acid tyrosine (represented by "Y") while peptide of SEQ ID NO. 22 includes the amino acid tryptophan (represented by the letter "W"). These two amino acids have ring structures and can be important in providing antioxidant activity. As such the present invention also includes peptides of the invention with extra added tyrosine and tryptophan residues.

Figure 11:
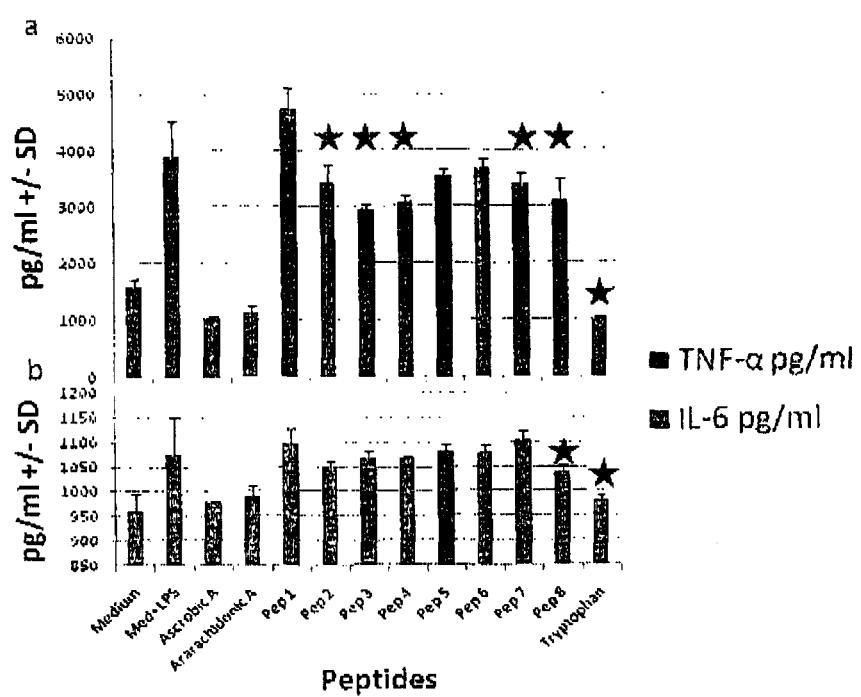
FIG. 11 illustrates the effects of peptides of fraction #23 and tryptophan on TNF-α and IL-6 expression in RAW 246.7 cells. All values expressed in pg/ml +/− SD. Cells grown in 24-well culture tissue-culture grade plates (Corning) and incubated with 100 μg/ml of one of eight milk peptides 1-8 (SEQ ID NOs. 28, 1, 29, 2, 8, 9, 19, and 22, respectively) and 1 μg/ml LPS. Values significantly lower than controls (p<0.05) are denoted by a star.

Furthermore, the Applicant was able to demonstrate the effects of peptides derived from human mother's milk on cytokine expression in a mouse macrophage cell line previously activated with lipopolysaccharide (LPS), a gram negative bacterial cell wall product which induces the expression of inflammatory cytokines, including TNF-α or IL-6, as well as interleukin-8 (IL-8), another pro-inflammatory cytokine [Baggiolini, M and Clark-Lewis. I. FEBS Letters, 307:97-101 (1992), Babu, P. B. R. et al. Clin Chim Acta 350: 195-200 (2004). As illustrated in FIG. 11, the Applicant has identified specific peptides in the mother's milk capable of significantly inhibiting or reducing the expression of tumor necrosis factor alpha (TNF-α) and interleukin-6 (IL-6) in cells that were previously induced to express inflammatory cytokines.

TNF-α and interleukin-6 are well-characterized pro-inflammatory cytokines. The significance of these findings is that the Applicant has identified several endogenous, human, milk peptides that are capable of inducing an anti-inflammatory immune response.

Figure 12:
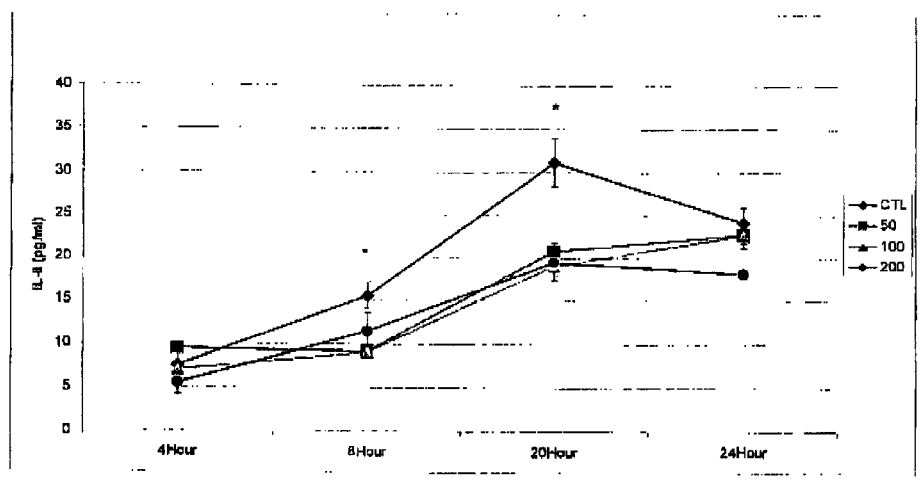
FIG. 12 illustrates the effects of peptide 23-8 (SEQ ID NO. 22) on LPS induced IL-8 expression in a Caeca cell culture model at 3 concentrations (50, 100, 200 μg/ml) at 4 different time points (4, 8, 20, 24 h). Culture medium for non-peptide treated cells was used as control. *P<0.05 indicates a significant difference between the 23-8 treated group and the control group (one-way ANOVA, n=4).
Figure 13:
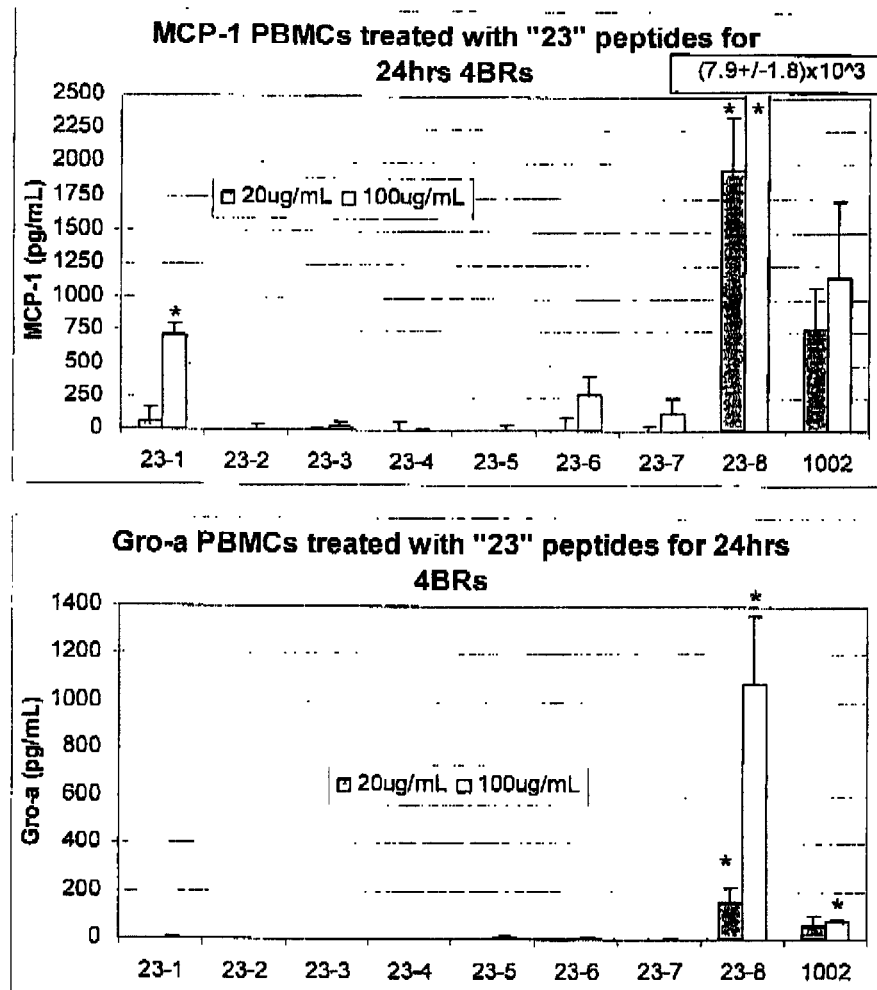
FIG. 13 illustrates stimulation of MCP-1 and Gro-a secretion from human peripheral blood mononuclear cells (PBMCs) after 24 h exposure to peptides 1-8 (SEQ ID NOs. 1, 29, 2, 8, 9, 19, and 22, respectively) from fraction #23. The experiment was carried out in 4 biological replicates (4 different donors), with 2 technical repeats in each biological experiment. The peptide fragments were tested at 2 concentrations, 20 and 100 μg/ml and MCP-1 and Gro-a were detected by sandwich ELISA kits (BioSource International and eBiosciences, respectively). A positive control peptide (1002) was used in the experiment.

The Applicant demonstrates in FIG. 12, that SEQ ID NO. 22 leads to a decrease in LPS induced interleukin-8 (IL-8) secretion in Caco-2 cells. The relevance to human health is that peptides may be efficacious as anti-inflammatory supplements in human milk and/or infant formula and other food solutions.

furthermore, the Applicant was able to demonstrate the effects of peptides derived from human mother's milk as immunomodulators. A standardized method of monitoring of immunomodulation by peptides is through monitoring of increased levels of cytokine/chemokine (e.g. growth regulated oncogene-alpha [gro-α] and monocyte chemoattractant protein 1 and 3 [MCP-1 and -3]) secreted from white blood cells after peptide exposure. One of the more robust readouts that have been demonstrated to correlate with increased immune protection is monocyte chemoattractant protein 1 (MCP-1) [Nijnik, A., et al. J. Immunol. 184; 2539-2550 (2010), Scott, M. G., et al. Nat Biotechnol. 25, 465 (2007)]. As illustrated in FIG. 13, the levels of MCP-1 from peripheral blood mononuclear cells (PBMCs) are significantly increased by peptide 23-8 (SEQ ID NO, 22). Peptide 23-1 (SEQ ID NO. 28) also showed significant activity. Up-regulation of MCP-1 expression demonstrates that peptides from fraction #23 may play a role as immunomodulators, as MCP-1 shows immunomodulation and can act as a protectant in endotoxin challenged animals [Zisman, D. A., et al. J. Clin. Invest. 99, 2832-36 (1997)].

Figure 14:
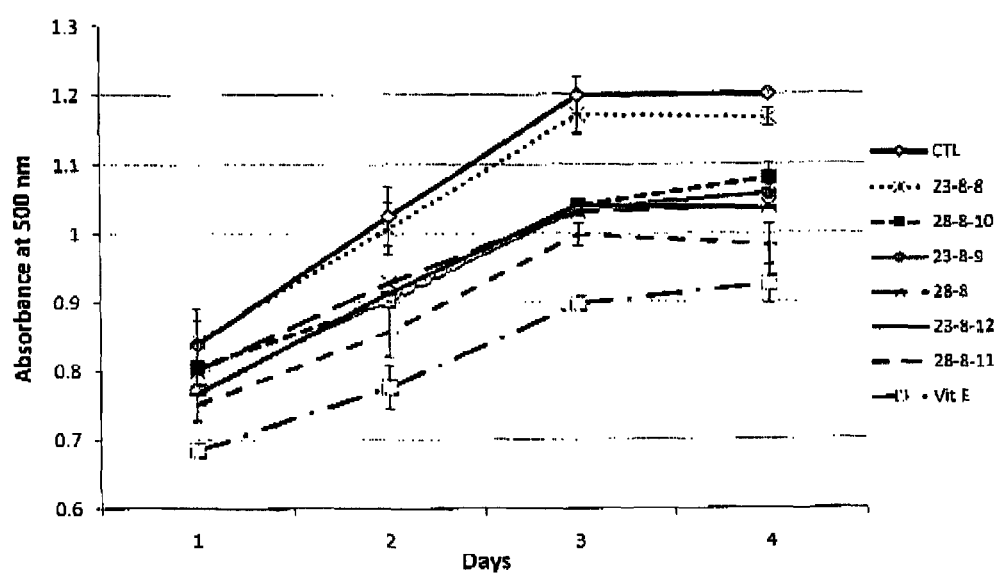
FIG. 14 illustrates a Linoleic acid emulsion assay of peptide ISELGW and its derivatives. All samples were analyzed at 250 μM. 23-8 (SEQ ID NO. 22), 23-8-8 (SEQ ID NO. 33), 23-8-9 (SEQ ID NO. 34), 23-8-10 (SEQ ID NO. 35), 28-8-11 (SEQ ID NO. 36), 23-8-12 (SEQ ID NO. 37).
Figure 15:
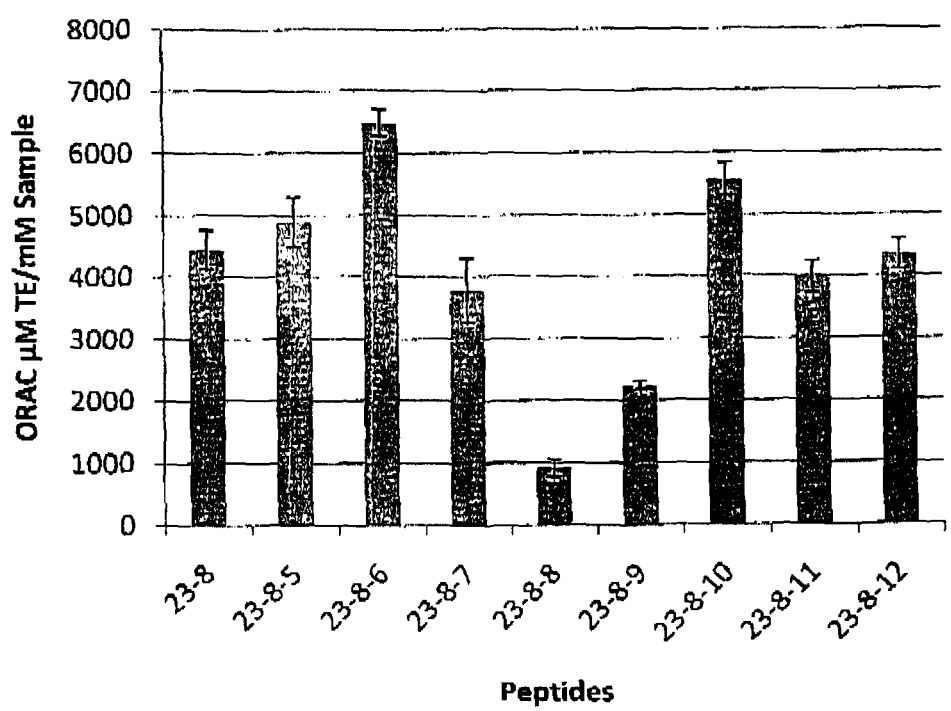
FIG. 15 illustrates ORAC values of synthetic peptides. 23-8 (SEQ ID NO. 22), 23-8-5 (SEQ ID NO. 30, 23-8-6 (SEQ ID NO. 31), 23-8-7 (SEQ ID NO. 32), 23-8-8 (SEQ ID NO. 33), 23-8-9 (SEQ ID NO. 34), 23-8-10 (SEQ ID NO. 35), 23-8-11 (SEQ ID NO. 36), 23-8-12 (SEQ ID NO. 37).

The Applicant also tested derivitives of SEQ ID NO. 22 (SEQ ID NO. 30 to SEQ ID NO. 37) for antioxidant activity. FIG. 14 shows that these peptides were capable of inhibiting the formation of hyperoxides in a linoleic acid emulsion assay, while FIG. 15 shows that the peptides were capable of scavenging reactive oxygen species and reducing oxidation during an ORAC assay.

The invention also encompasses therapeutic strategies that involve targeting stimulators of the oxidative stress pathway, disrupting the formation of complexes that stimulate the oxidative stress pathway, modulating an immune response. These methods may be used in combination with other known therapies for treating conditions related to oxidative stress, inflammation and pathogenic infections.

The invention also encompasses therapeutic strategies that involve targeting the oxidative stress signaling pathways to downregulate the production of oxidative stress and pro-inflammatory mediators or disrupting the formation or complexes that stimulate oxidative stress process. These methods may be used in combination with other known therapies for treating an oxidative stress process.

In humans, oxidative stress is involved in many diseases, such as atherosclerosis, Parkinson's disease, heart failure, myocardial infarction, Alzheimer's disease and chronic fatigue syndrome. As such, the instant invention also encompasses methods for the treatment of oxidative stress related diseases in a subject comprising the administration to the subject of a therapeutic composition comprising one or more of the peptides of the invention and a pharmaceutically acceptable carrier to inhibit the expression and resulting activity of oxidative stress mediators, or to enhance the activity of cellular antioxidants. Examples of cellular antioxidants include, without limitation, glutathione (GSH), superoxidase dismutase (SOD), catalase, thioredoxin reductase, glutathione reductase (OR), glutathione preoxidase, glutathione S-transferase (OST), γ-glutamylcysteine synthetase and glutathione synthetase.

The peptides of the invention may be labeled with a label to facilitate their detection in a variety of assays as is understood by one of skill in the art. Such labels may include but are not limited to radioactive label and fluorescent label. The peptides of the invention may be provided with a carrier such as for example couple to bovine serum albumin (BSA) or keyhole limpet haemocyanin. The peptides may be covalently or non-covalently coupled to a solid carrier such as a microsphere of gold or polystyrene, a slide, chip or to a wall of a microtitre plate. The peptide may be labeled directly or indirectly with a label selected from but not limited to biotin, fluorescin and an enzyme such as horseradish peroxidase.

According to another aspect, the present invention relates to a composition for maintaining cells, tissues and/or organs in a viable state ex vivo during storage and in vivo during reperfusion, wherein said composition comprises one or more peptides, wherein said peptides are selected from the group comprising of SEQ ID NOs. 1 to 37.

When organs are harvested for transplantation, the ensuing period of hypoxia, followed by reperfusion of the organ, is accompanied by substantial tissue damage, including cell apoptosis and parenchymal dysfunction. Such ischemia/reperfusion (I/R) injury can involve inflammatory reactions that result in the creation of free radicals that further damage the organ.

One or more peptides selected from the group comprising of SEQ ID NOs. 1 to 37 can be added to an organ storage or perfusion solution to increase the viability of the cells, tissues and/or organs for transplantation. Storage/reperfusion solutions that can be used with the peptides of the invention include any solution for maintaining viability of a cell, tissue or organ. Examples of storage or perfusion solutions include, without limitation, University of Wisconsin (UW) solution (Viaspan®, Dupont Pharma, Wilmington, Del.), Euro-Collins solution and Ringer's solution. The UW solution, is described in U.S. Pat. Nos. 4,798,824 and 4,879,283.

In another embodiment, monoclonal antibodies that recognize any of the peptides of the invention may also be made and used to detect the presence of the peptides in a sample. This provides a rapid and simple method of testing human milk for its quality. In general, methods for the preparation of antibodies are well known. For example, methods to produce monoclonal antibodies which specifically recognize the peptides of the invention, are well known to those of skill in the art. In general, peptides are injected in Freund's adjuvant into mice. After being injected 9 times over a three week period, the mice spleens are removed and resuspended in phosphate buffered saline (PBS). The spleen cells serve as a source of lymphocytes, some of which are producing antibody of the appropriate specificity. These are then fused with a permanently growing myeloma partner cell, and the products of the fusion are plated into a number of tissue culture wells in the presence of a selective agent such as HAT. The wells are then screened to identify those containing cells making useful antibody by ELISA. These are then freshly plated. After a period of growth, these wells are again screened to identify antibody-producing cells. Several cloning procedures are carried out until over 90% of the wells contain single clones which are positive for antibody production.

From this procedure a stable lines of clones is established which produce the antibody. The monoclonal antibody can then be purified by affinity chromatography using Protein A or Protein G Sepharose (see also, U.S. Pat. Nos. 4,609,893; 4,713,325; 4,714,681; 4,716,111; 4,716,117; and 4,720,459).

The above disclosure generally describes the present invention. A more complete understanding can be obtained by reference to the following specific Examples, These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Example 1

Chemicals

Pepsin P7000, pancreatin P1750, bile salts 8333, 6-hydroxy-2,5,7,8-tetramethylchroman-2-carboxylic acid (Trolox), 2,2'-Azobis (2-amidinopropane) dihydrochloride (AAPH), rutin trihydrate, trifluoroacetic acid (TFA), acetic acid (ACS grade), sodium bicarbonate, L-tryptophan (Trp), and potassium phosphate mono- and di-basic were purchased from Sigma-Aldrich Canada Ltd (Oakville, Ontario). Methanol and acetonitrile (HPLC grade) and Fluorescein were purchased from Fisher Scientific Canada (Ottawa, Ontario). High-purity water was produced in the laboratory by an Alpha-Q system (Millipore, Marlborough, Mass.).

Example 2

Human Milk Samples

Samples of mature human milk (HM) were obtained from volunteer mothers whose milk was expressed. Samples were stored by mothers in a −20° C. freezer and transported to Applicant's laboratory on dry ice. Once in the laboratory, the HM was freeze-dried and stored at −80° C. until ready for analysis.

Example 3

Digestion of Human Milk

The solid content of HM accounts for a$_{ppr}$oximately 13% of total weight [Shehadeh N. et al. The J Pediatrics 148:122 (2006)]. Based on this composition, 130 g of freeze-dried HM was diluted with 870 mL of deionised water. The digestion model mimicking premature infant digestion was modified from that utilized by Etcheverry [Etcheverry P, et al. J Dairy Sci 2004; 87:3629 (2004)].

i. Gastric digestion: To mimic the gastric digestion of the premature infant, the sample was further diluted with physiological concentrations of salts [Etcheverry P, et al. .1 Dairy Sci 2004; 87:3629 (2004)] (530 mL of 140 mM Nacl plus 5 mM KCl). The pH was adjusted to 5.5 with 1 M HCl, then 76 mL of pepsin (Sigma P7000, 4 g in 100 mL of 0.1 M HCl) was added and the final pH was adjusted to 4.0. The sample was incubated for 30 minutes at 37° C. and 100 rpm on a MaxQ 4000 incubator (Barnstead Lab-Line), then adjusted to pH 6.0 and incubated for another 30 minutes.

ii. Intestinal digestion: After gastric digestion, 380 mL of pancreatin (0.8 g) and bile salts (4.8 g) were prepared in 400 mL of 0.1 M NaHCO$_3$ and were added together. The pH was adjusted to 7.0 with 1 M NaHCO$_3$ and the solution incubated for 2 hours at 37° C. The sample solution was heated in a water bath at 90° C. for 15 minutes to inactivate the enzymes (pancreatin and bile salts).

iii. Removal of lipid: The digested HM sample was stored at +4° C. overnight in a separatory funnel to separate the lower phase containing the peptides from the upper phase containing the lipids.

Example 4

Separation of Peptides in Digested Human Milk i. Membrane Filtration

An Amicon stirred cell unit 8400 and a 3000 Da molecular cut-off membrane (Millipore, Billerica, Mass.) was used to separate the peptides into low (<3000 Da) and high molecular weight (>3000 Da) filtrates. The low molecular weight filtrate (<3000) was freeze dried and then stored at −80° C. until preparative HPLC separation.

ii. HPLC Separation
a. Column: Symmetry 300 C18 (5 µm 19×250 mm) from Waters Corporation.
b. Solvent: Linear gradient 0-70% B in 60 min at a flow rate of 6.0 mL/min; A: 0.05% TFA in water, B: 0.5% TFA in acetonitrile.
c. Detector: Waters PDA 996 set at 214 nm.
d. HPLC system: Waters 600E Multisolvent Delivery System.
e. Fraction collection: The Waters Fraction Collector III was used to collect fractions every min (6 ml) and a total of 55 fractions were collected and combined from different runs. These fractions were freeze-dried and used for the ORAC assay.

Example 5

Oxygen Radical Absorbance Capacity (ORAC) of HPLC Fractions

This assay measures the scavenging capacity of antioxidant nutrients against the peroxyl radical [Diehl-Jones W L and Askin D F. American Association of Critical Care Nurses (AACN) Clin Issues 15: 83 (2004)], which is one of the most common reactive oxygen species (ROS) in the human body. Out of all fractions collected and tested, fraction #23 was found to have the highest ORAC value (5274±630 uM Trolox eq/g sample) (FIG. 1), which was about 65 times higher than the whole HM sample. To identify the peptides in fraction #23, the sample was injected into an LC-MS/MS system.

Example 6

Identification of Peptides in ORAC Active HPLC Fraction

Figure 2:
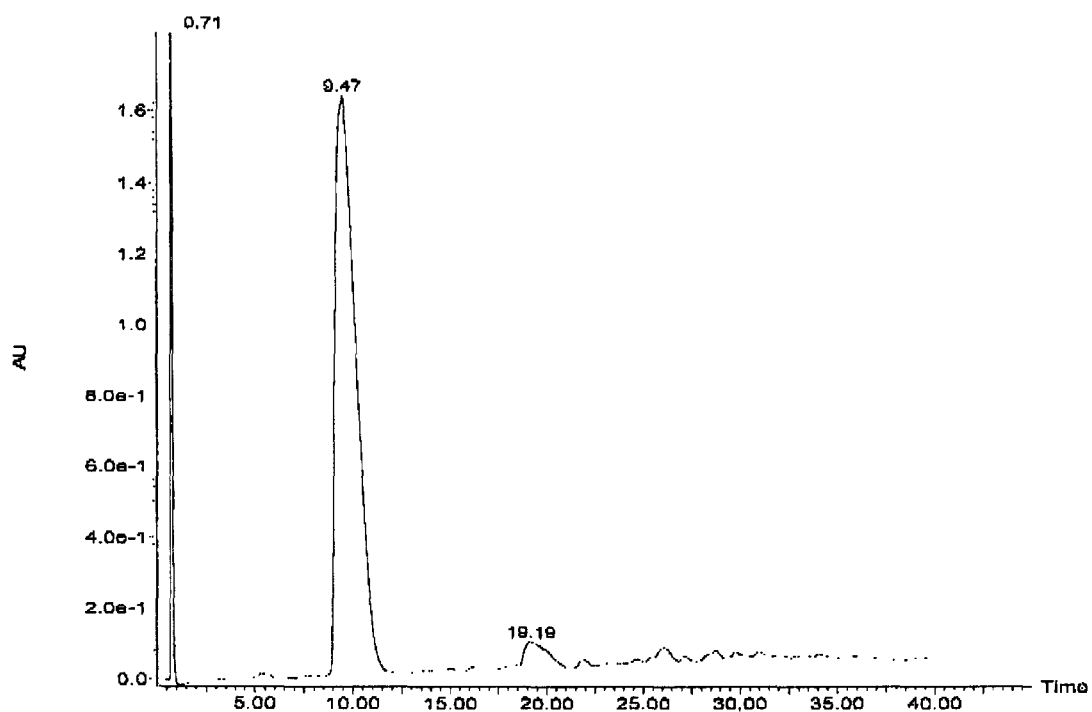
FIG. 2 illustrates UV chromatogram of fraction #23 from Acquity UPLC system; Column: Acquity BEH C18 1.7 uM, 2.1×100 mm; Eluent: linear gradient 0-10% acetonitrile in water for 40 min; Detector: PDA at 214 nm. The major UV peak at RT 9.47 was identified as tryptophan by LC-MS/MS and by comparison with standard L-Tryptophan.
Figure 3:
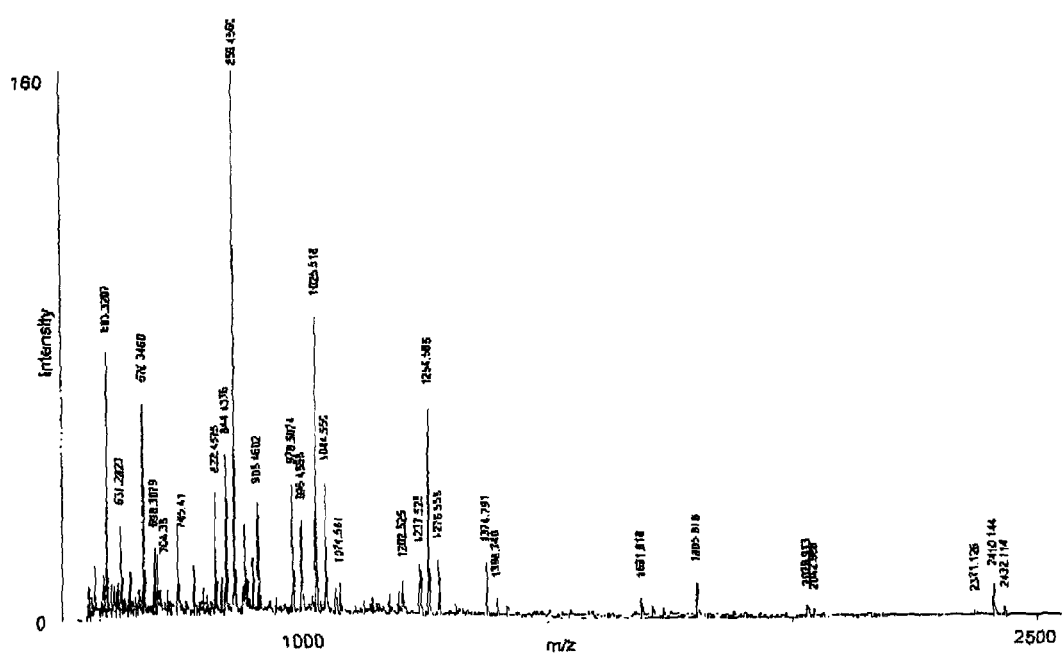
FIG. 3 illustrates Mass spectrum of fraction obtained from a MALDI Q-TOF instrument. Each peak of this spectrum was selected for MS/MS analysis followed by de novo sequencing using PepSeq 1.2 or Mascot MS/MS ion online search.

The active fraction #23 (1 mg/ml) was injected into the Waters Acquity™ UPLC system coupled to a Waters Micromass Quattro Micro API and a MALDI Q-TOF mass spectrometer. The UV chromatogram of fraction #23 is shown in FIG. 2 and its mass spectrum (Q-TOF) in FIG. 3. Peaks from the MS were subjected to MS/MS analysis on both Quattro Micro API and Q-TOF instruments. The peak lists were generated and submitted to Mascot MS/MS ion online search from Matrix Science Inc (http://www.matrixscience.com) or analyzed using PepSeq software version 1.2 [Rosenski J. et al. Organ Mass Spectrom. 29(11):654 (1994)]. The peptides identified as fragments from human beta casein Eire the peptides included in the Sequence Listing as SEQ ID NOs. 1 to 7 and SEQ ID NOs. 28 and 29. The peptides identified as fragments from human kappa casein are the peptides included in the Sequence Listing as SEQ ID NOs. 8 to 10. In addition, peptides included in the Sequence Listing as SEQ ID NOs. 11 to 25 were identified in fraction #23 but not found to be fragments of known human milk protein.

Examples or MS/MS spectra are shown in FIGS. 5-10.

Example 7

Peptide Synthesis

Eight of the peptides identified in fraction #23 (SEQ ID NOs. 1, 2, 8, 9, 19, 22, 28 and 29) and eight derivitives of SEQ ID NO. 22 (SEQ ID NOs. 30 to 37) were synthesized by GenWay Biotech Inc (San Diego, Calif., USA).

Example 8

Oxygen Radical Absorbance Capacity of Fraction and Selected Peptides

The synthesized peptides of example 7 were evaluated for their antioxidant potential using the ORAL assay (FIG. 4). No scavenging activities were observed for peptides VPVQA (SEQ ID NO. 1) and PLAQPA (SEQ ID NO. 29). Peptide HNPI (SEQ ID NO 28; 114 ±14 uM Trolox/g) showed relatively weaker scavenging properties compared to the five other compounds tested. The three peptides SEQ ID NO. 2, SEQ ID NO. 8 and SEQ ID NO. 9 have very similar activities, 3940±623, 3462±560, and 3380±592 uM Trolox/g of peptide, respectively. The two most active peptides were SEQ ID NO. 19 (8205±552 uM Trolox/g) and SEQ ID NO. 22 (6372±354 uM Trolox/g) with scavenging activities higher than fraction No. 23. The peptides with radical scavenging properties appeared to contain either the amino acid tyrosine (represented by Tyr) or amino acid tryptophan (represented by Trp). These two amino acids have ring Structures that might be important in providing the antioxidant activity.

Example 9

Effects of Human Milk Peptides on Cytokine Expression in Vitro

A mouse macrophage cell line (RAW 264.7) was activated with 1 µg/ml lipopolysaccharide (LPS), a gram negative bacterial cell wall product which induces the expression of inflammatory cytokines (Interleukin-6 [IL-6] and Tumor Necrosis Factor alpha [TNF-α]) via activation of toll-like receptors [Wu, T. T. et al. Toxicol Let. 195-202 (2009). After incubation with LPS for 24 hours in the presence of the peptides from example 7, cell supernatant was collected and mouse IL-6 and TNF-α titres were determined by a standard micro-plate enzyme-linked immunosorbent assay (ELISA) technique (e-Biosciences).

As illustrated in FIG. 11, (a) Peptides 2, 3, 4, 7, and 8 (SEQ ID NOs. 1, 29, 2, 19, and 22 respectively) significantly inhibited TNF-α expression compared to the control (cell culture medium plus LPS) and 100 µM tryptophan elicited the greatest inhibition of TNF-α. (b) Peptide 8 (SEQ ID NO. 22) significantly reduced IL-6 expression.

Example 10

Cell Culture Experiments with Infant Intestinal Cells (FHS)

Cell culture experiments with infant intestinal cells (FHS) are carried out to determine if pre-treatment with the novel peptides upregulate antioxidant protection in vitro.

Treat FHS 74 Int with/without peptide enriched medium for 4, 12 hours or 24 hours (could be done on one plate with staggered amounts). Wash-out extra peptide (go back to basal levels), then load 30 with 10 uM H2DCFDA. Wash-out dye. Challenge with and without peroxide (1 mM). Read fluorescence at 0, 30 min, 1 hour, 2 hours, and 3 hours. Test viability at end of experiment with trypan blue Variables: 1. Peptide concentration (0, 20 uM, 100 uM); 2. Time (0, 4, 12, 24 hrs); and 3. ±IF gamma.

Example 11

Ability of Peptides to to Prevent Lipid Peroxidation

The activities of the peptides of the invention and modified peptides by addition of phosphorus and acetyls groups may be further evaluated for their ability to prevent lipid oxidation and for their ability to reduce oxidative stress in cell culture and in TPN solutions.

To further confirm the ability of the peptides of the invention to reduce oxidative stress the following experiments may be performed:

The capacity of the peptides to inhibit lipid peroxidation is measured in a linoleic acid emulsion system and compared to α-tocopherol and butylated hydroxyl toluene (BHT) using established methods [Zhu K. Process Biochemistry 41:1296 (2006); Osawa T, Namiki M. J. Agric. Food Chem. 33: 777 (1985)]. Each peptide is dissolved in phosphate buffer (pH 7.0) and added to a solution of linoleic acid in 99.5% ethanol. The mixtures are incubated at 50° C. in the dark, and the degree of oxidation is evaluated by measuring the ferric thiocyanate values [Osawa T, Namiki M. J. Agric. Food Chem. 33: 777 (1985)]. Peptides may also be added to human milk and infant formations. The milks with and without added peptides are left at room temperature for 4 hours and then lipids extracted and lipid hydroperoxides measured by FOX assays [Firth C A. et al. Free Radic. Res. 41 :839 (2007)].

The results from assay seen in FIG. 12 proves that the peptides of the present invention can effectively prevent lipid peroxidation in human milk and infant formulas

Example 12

Immunomodulatory Properties of Peptides Derived from Human Milk

Applicant has collected data indicating a correlation between elevated cytokine/chemokine responses in human Peripheral Blood Mononuclear Cell (PBMC) treated with a peptide of the invention for 24 hours and the peptides ability to protect in vivo models. The data have demonstrated that peptide SEQ ID NO. 22 and SEQ ID NO. 28 are triggering a robust response of monocyte chemoattractant protein-1 (MCP-1), which is one of the lead chemokines examined in these type of screens. A broader set of cytokine/chemokines may be investigated in, concurrent with host cell toxicity assays, to confirm the properties of the peptides.

Cell Isolation and Peptide Stimulation

Venous blood from healthy volunteers is collected in Vacutainer® collection tubes containing sodium heparin as an anticoagulant (BD Biosciences). Blood is diluted with an equal volume of complete RPMI 1640 medium, supplemented with 10% (v/v) heat-inactivated FBS, 2 mM L-glutamine, and 1 mM sodium pyruvate (all from Invitrogen Life Technologies) and separated by centrifugation over a Ficoll-Paque Plus (Amersham Biosciences) density gradient. The buffy coat is collected and washed twice in RPMI 1640 complete medium, and the number of PBMCs can be determined by trypan blue exclusion. Peripheral Blood Mononuclear Cells (PBMC) ($5 \times 10^5$) are seeded into 24-well tissue culture dishes (Falcon; BD Biosciences) at $1 \times 10^6$ cells/mL at 37° C. in 5% $CO_2$, and rested for 1 h. The cells are then exposed to peptides of the invention at 50 µg/mL for 24 hrs. All experiments involve at least three to five biological replicates. The red blood cells are left at the bottom of the Ficoll-Paque Plus density gradient and these are pooled together, washed 3 times in saline and used for hemolysis assay/toxicity testing.

Detection of Cytokines

Following 24 hrs of peptide exposure, the tissue culture supernatants are centrifuged at 16,000G (13,000 rpm) at 4° C. for 5 minutes in an IEC MicroMax centrifuge to obtain cell-free samples. Supernatants are aliquoted and then stored at −20° C. before assay for various cytokines/chemokines. Cytokines/chemokines are detected by sandwich ELISA kits (BioSource International or eBiosciences) and multiplex kit (Luminex). All assays are performed in triplicate. The concentration of the cytokines/chemokines in the culture medium can be quantified by establishing a standard curve with serial dilutions of the recombinant human cytokines/ chemokines. Secretion of TNF-α will also be monitored in rested PMBCs and cells exposed to peptide and/or LPS (*P. aeruginosa*) by capture ELISA after 24 hrs (eBiosciences).

Example 13

New strategies to Protect Total Parenteral Nutrition (TPN) Solutions Against Photo-Oxidation The absence of adequate photo-protection of TPN solutions, as observed in neonatal units in Canada, leads to excitation of riboflavin that generates singlet oxygen or superoxide anion. In presence of ascorbate or amino acids these ROS favor the production of $H_2O_2$ and in presence of lipids; aldehydes such as HNE are formed. Since from the previous examples tryptophan and peptides of this invention have a free radical scavenging property, the peptides of this invention may be able to scavenge the singlet oxygen as well as the superoxide anion and therefore, prevent the generation of peroxides and aldehydes, thereby protecting TPN solutions against photo-oxidation.

The peptides of this invention can be used, therefore, in the manufacture of new formulations of TPN to prevent the photo-oxidation of TPN components, leading to the improvement of the health of infants on TPN.

1) Assess the efficiency of and peptides to quench singlet oxygen or superoxide anion generated by light exposition of riboflavin. In absence of reducers, riboflavin is destroyed by singlet oxygen and superoxide anion induced by light-excitation of the riboflavin. Therefore, this objective is achieved by following the disappearance of riboflavin in a solution containing riboflavin alone in presence or not of tryptophan and/or peptides.
2) Assess the efficiency of peptides to prevent the generation of peroxides and aldehydes in TPN solution devoid of photo-protection. The objective is reached by measuring peroxides and HNE in TPN solutions devoid of photo-protection but containing or not tryptophan and/or peptides.
3) Verify the chemical structure of peptides after they have exerted their antioxidant activities. The objective is attained by a mass spectrometry study of these compounds after incubation with singlet oxygen/superoxide anion (by incubation with light-exposed riboflavin), $H_2O_2$ and HNE.
4) Test if ascorbate recycles the oxidized tryptophan/peptides. This test is achieved by measuring these compounds on MS following their incubation with light-exposed riboflavin, $H_2O_2$ or HNE in presence or not of ascorbate.
5) Verify the optimum concentration of peptides to be used in order to prevent the photo-oxidation of TPN solutions. The aim is reached by using different concentrations of these compounds, alone or in presence of different components of TPN, to prevent ROS generation.

Example 14

Prophetic Protocol for Storing Organs for Transplantation

An organ for transplantation is removed from a donor and stored in cold (4° C.) ViaSpan™ solution containing one or more peptides selected from the group comprising of SEQ ID NOs. 1 to 29 prior to transplantation. The organ is carried to the OR immersed in the ViaSpan™ solution containing one or more peptides selected from the group comprising of SEQ ID NOs. 1 to 29 and kept in the solution until transplantation.

The invention claimed is:

1. An isolated peptide wherein:
   (a) the peptide consists of a sequence selected from the group consisting of SEQ ID NO. 11 to SEQ ID NO. 27 and SEQ ID NO. 30 to SEQ ID NO. 37; or
   (b) the peptide comprises at least two sequences selected from SEQ ID NO. 11 to SEQ ID NO. 27 and SEQ ID NO. 30 to SEQ ID NO. 37, wherein the at least two sequences may be the same or different.

2. The isolated peptide of claim 1, which consists of a sequence selected from the group consisting of SEQ ID NOs. 19, 22, and 30 to 37, or which comprises at least two sequences selected from the group consisting of SEQ ID NOs. 19, 22, and 30 to 37 wherein the at least two sequences may be the same or different.

3. A pharmaceutical composition comprising one or more peptides according to claim 1 and a pharmaceutically acceptable carrier.

4. A pharmaceutical composition for the treatment of a condition related to oxidative stress, comprising one or more peptides according to claim 1 and a pharmaceutically acceptable carrier.

5. A method for treating an oxidative stress condition in a subject, comprising administering to the subject an effective amount of the pharmaceutical composition according to claim 3.

6. The method of claim 5, wherein the pharmaceutical composition comprises at least one peptide of claim 2.

7. A method for treating an inflammatory reaction in a subject, comprising administering to the subject an effective amount of the pharmaceutical composition according to claim 3.

8. A method for treating a pathogenic infection in a subject, comprising administering to the subject an effective amount of the pharmaceutical composition according to claim 3.

9. A method for supplementing a diet of a neonate subject, comprising administering to the neonate subject a composition comprising one or more peptides according to claim 1.

10. A food or food solution, comprising one or more peptides according to claim 1.

11. A nutraceutical composition, comprising one or more peptides according to claim 1.

12. A Parenteral Nutrition (PN) solution, comprising one or more peptides according to claim 1.

13. A composition for maintaining cells, tissues and/or organs in a viable state ex vivo during storage or in vivo during perfusion, comprising one or more peptides according to claim 1.

14. The isolated peptide according to claim 1, wherein the peptide is derived from human milk.

15. The isolated peptide of claim 1, which consists of a sequence selected from the group consisting of SEQ ID NOs. 19 and 22, or which comprises two or more sequences selected from the group consisting of SEQ ID NO. 19 and SEQ ID NO. 22 wherein the two or more sequences may be the same or different.

16. The pharmaceutical composition of claim 3, comprising at least one peptide of claim 15.

17. The nutraceutical composition of claim 11, comprising at least one peptide of claim 15.

18. The PN solution of claim 12, comprising at least one peptide of claim 15.

* * * * *